Patent Number: 5,917,023
Date of Patent: Jun. 29, 1999

[54] REDUCTIVE COUPLING OF NITROBENZENE OR NITROBENZENES SUBSTITUTED ON THE NUCLEUS TO GIVE THE CORRESPONDING AZOBENZENES AND AZOXYBENZENES BY MEANS OF REDOX CATALYSTS

[75] Inventors: Alfred Hagemeyer, Rheine; Daniel Heineke, Ludwigshafen; Guido Voit, Schriesheim; Tom Witzel, Ludwigshafen, all of Germany

[73] Assignee: BASF Aktiengesellshcaft, Ludwigshafen, Germany

[21] Appl. No.: 08/869,760

[22] Filed: Jun. 5, 1997

[30] Foreign Application Priority Data

Jun. 5, 1996 [DE] Germany ............................ 196 22 644
Aug. 20, 1996 [DE] Germany ............................ 196 33 552

[51] Int. Cl.⁶ ........................ C07C 245/08; C07C 291/08
[52] U.S. Cl. ............................. 534/572; 534/585
[58] Field of Search .................. 534/585, 572; 502/353

[56] References Cited

U.S. PATENT DOCUMENTS

| | | | |
|---|---|---|---|
| 1,451,489 | 4/1923 | Brown et al. ............................ | 534/572 |
| 3,041,377 | 6/1962 | Harast .................................. | 534/585 X |
| 3,578,720 | 5/1971 | Dodman et al. ......................... | 534/572 |
| 3,700,605 | 10/1972 | Dodman et al. ........................ | 502/324 |
| 3,989,764 | 11/1976 | Wooley .................................. | 568/949 |
| 4,265,834 | 5/1981 | Birkenstock et al. .................. | 564/421 |
| 5,689,005 | 11/1997 | Hagemeyer et al. ................... | 564/420 |

OTHER PUBLICATIONS

Finholt et al., *J. Am. Chem. Soc.*, vol. 77, p. 4163, 1955.
Meier et al., *Chem. Ber.*, vol. 89, pp. 2301–2305, 1965.
Ohe et al., *J. Org. Chem.*, vol. 54, No. 17, pp. 4169–4174, 1989.
Gellner et al., *J. Chem. Soc.*, pp. 1145–1148, 1949.
Kmiewcik, *J. Org. Chem*, vol. 30, pp. 2014–2020, 1965.
Lin et al., *J. of Xiamen University*, vol. 25, No. 4, Jul. 1986, pp. 449–455.
Konishi et al., *Chem. Lett.*, vol. 11, pp. 1351–1354, 1980.

*Primary Examiner*—Fiona T. Powers
*Attorney, Agent, or Firm*—Keil & Weinkauf

[57] ABSTRACT

Nitrobenzene or a nitrobenzene substituted on the nucleus is subjected to reductive coupling to give the corresponding azobenzene and azoxybenzene under heterogeneous catalysis with substantial avoidance of overreduction to aniline derivatives by means of a redox catalyst in its reduced or partly reduced form, the redox catalyst containing at least one active metal component capable of a change of oxidation state.

10 Claims, 2 Drawing Sheets

REDUCTIVE COUPLING OF NITROBENZENE OR NITROBENZENES SUBSTITUTED ON THE NUCLEUS TO GIVE THE CORRESPONDING AZOBENZENES AND AZOXYBENZENES BY MEANS OF REDOX CATALYSTS

The invention relates to a process for the reductive coupling of nitrobenzene or nitrobenzenes substituted on the nucleus under heterogeneous catalysis to give the corresponding azobenzenes and azoxybenzenes with substantial avoidance of overreduction to aniline derivatives by means of a redox catalyst in its reduced or partly reduced form, the redox catalyst containing at least one active metal component capable of a change of oxidation state. In one embodiment of the present invention, the above process is carried out in the presence of water. In the description, the term nitrobenzene includes both nitrobenzene as such and nitrobenzenes substituted on the nucleus. The novel reductive nitrobenzene coupling can be carried out by a steady-state as well as a non-steady-state reaction.

Azobenzene and azoxybenzene are important intermediates in the chemical industry and are used, inter alia, in the synthesis of antioxidants, dyes, active ingredients, polymer modifiers, adhesives and sealing compounds, photoresists and photosensitive systems.

Accordingly, the prior art also discloses the reduction of nitrobenzene to azobenzene and/or azoxybenzene, azobenzene conventionally being prepared by diazotizing aniline and reacting the diazonium salt with benzene in the liquid phase (cf., among many references, Finholt, Jacobsen, Ogard and Thomsen in J. Am. Chem. Soc. 77 (1955), 4163, Meier and Bohler in Chem. Ber. 89 (1965), 2301, and Ohe, Uemura, Sugita, Matsuda and Taga in J. Org. Chem. 54(17) (1989), 4169–4174).

Disadvantages of these reactions are the very expensive reduction reagents which cannot be regenerated and which have to be used in superstoichiometric amounts. In most of these processes, moreover, large amounts of salts are obtained, which is also disadvantageous.

The first reductions of the gas phase are described by Buckley et al. in J. Chem. Soc. (1949), 1146–46 and by Kmiecik in J. Org. Chem. 30 (1965), 2014–2020. Buckley et al. describe the reduction of nitrobenzene to azobenzene without a catalyst by heating nitrobenzene for 24 hours at 250° C. under a CO pressure of 3000 atm, azobenzene being obtained in a yield of 97.5%. At 200° C. or at below 2500 atm, virtually no reduction took place. Kmiecik describes the reduction of nitrobenzene to azobenzene with CO in the presence of iron pentacarbonyl catalysts in dry benzene. At about 200° C. and CO pressures of about 3000 psig ($\hat{=}$207 bar) and with reaction times of about 3 hours, azobenzene yields of up to 80% were obtained.

However, these two processes have disadvantages in that they must be carried out at very high CO pressures and for long reaction times.

Processes for the reduction of nitrobenzene under heterogeneous catalysis to give azobenzene and/or azoxybenzene in the gas phase are also known.

For example, Lin et al. in Ziran Kexueban 25(4) (1986), 449–455, describe the interaction of CO with nitrobenzene over metal oxide catalysts selected from the group consisting of $CuO$, $MoO_3$, $V_2O_5$ and $PdO$, each on $SiO_2$ carriers. In these reactions, CO is oxidized to $CO_2$ while nitrobenzene is reduced to various N-containing compounds, phenazine and azobenzene also being formed. This reaction has in particular the disadvantage that, owing to the acidic $SiO_2$ carrier and the active metal in the form of a Lewis acid compound, many secondary reactions occur and all that is obtained is a complex product mixture, the selectivity for azobenzene being low.

Konishi et al., in Chem. Lett. 11 (1980), 1351–1354, describe the deoxygenation of nitrobenzene to azobenzene by contact with a carbon catalyst which was impregnated with $K_2CO_3$. This process has the disadvantage that the carbon is gradually consumed by oxidation to oxides of carbon and the catalyst becomes less mechanically stable. In this process, the carbon is thus a stoichiometric reduction reagent which cannot be regenerated. The reaction is therefore strictly not a heterogeneous catalysis but a stoichiometric fluid-solid reaction.

German Laid-Open Application DOS 1,810,828 (ICI, 1969) describes the continuous, steady-state reduction of nitrobenzene to predominantly nitrosobenzene, but also to azoxy- and azobenzene with CO in the gas phase over catalysts which contain two or more of the heavy metals Ti, V, Cr, Mn, Fe, Co, Ni, Cu, Ge, Zr, Mo, Ag, Sn, Sb, La, Ce, Nd, Ta, W, Re, Au, Hg, Tl, Pb, Bi and Th in the form of their oxides, hydroxides, carbonates or phosphates. Preferred heavy metal pairs are Pb-Mn for the preparation of nitroso compounds, Co-Mn for the preparation of nitroso compounds or azoxybenzene compounds and Cu-Ce for the preparation of azo compounds.

According to this Laid-Open Application, Ag-Mn-O on a ceramic carrier (pumice) and a feed of nitrobenzene and CO give azobenzene and nitrobenzene in a ratio of 3:7 in the condensate.

With Co-Mn-O on pumice and a feed of nitrobenzene and CO, azoxybenzene and nitrobenzene in a ratio of 3:7 are obtained in the condensate.

With Ce-Fe-O on pumice, a mixture of azoxybenzene and azobenzene and unconverted nitrobenzene are obtained with a nitrobenzene conversion of 20%.

With Ce-Cu-O on pumice and with different Ce/Cu ratios, from 55 to 72% of azobenzene and from 6.5 to 14% of azoxybenzene, based in each case on the nitrobenzene introduced, were found in the condensate.

When Ce-Bi-O was used, only very low activity with a conversion of only from 5 to 10% was found.

When Fe-Cu-O on pumice was used, a nitrobenzene conversion of 56% was achieved, many other products, eg. diphenylurea, being found in the condensate in addition to azobenzene and azoxybenzene.

The use of Mn-Ni-Co-O on pumice gave a mixture of azobenzene and azoxybenzene in the condensate at a conversion of almost 50%.

On the other hand, with Mn-Co-O, Mn-O, Fe-Mn-O, Ce-Fe-O, Ce-Mn-O and Pb-Mn-O on C and Ag-Mn-O on pumice, nitrosobenzene was obtained as the main product.

With Cu-Ce-O on pumice, a mixture of nitrosobenzene and azobenzene was obtained in the fluidized bed at a nitrobenzene conversion of 20%. The use of Fe-Mn-O on pumice gave a mixture of azobenzene, azoxybenzene and nitrosobenzene at a nitrobenzene of about 25%.

The disadvantage of the above German Laid-Open Application 1,810,828 is the incomplete, generally very low nitrobenzene conversion (from 5 to 56% according to the Examples) and the consequently poor yields of azobenzene and azoxybenzene, which entail expensive separation of substances and recycling of nitrobenzene. Moreover, according to this German Laid-Open Application, only very small catalyst space velocities are used, resulting in correspondingly low space-time yields (1 g of nitrobenzene/h with 12 g of catalyst material, which corresponds to a WHSV (Weight Hourly Space Velocity) of 0.08 h$^{-1}$). Furthermore, the active metal components of the catalysts used are present in reduced form only in a small proportion at the surface or were for the most part not subjected to any preliminary reduction at all.

As is evident from the above summary, the reduction of nitrobenzene to azobenzene and/or azoxybenzene has been carried out to date by either homogeneous or heterogeneous catalysis in the liquid phase or without a catalyst or by heterogeneous catalysis in the gas phase using unreduced or slightly reduced catalysts in a steady-state reaction.

It is an object of the present invention to provide a catalyst and a process for the reduction of nitrobenzene to azobenzene and azoxybenzene, which is readily controllable and monitorable, permits simple heat transport in process engineering terms during the reaction and achieves high, possibly even quantitative, nitrobenzene conversions in combination with high selectivity for azobenzene and azoxybenzene, tolerates high nitrobenzene catalyst space velocities, produces no carbonylation byproducts, such as isocyanates/carbamates/urethanes and moreover results in only very little overreduction by hydrogenation to aniline and produces no significant amounts of nitrosobenzene in the product mix and permits operation under relatively low pressures of <100 bar of the gaseous reducing agents used and may even permit a procedure at atmospheric pressure.

Steady-state reaction

We have found that these objects are achieved, in the case of a steady-state reaction, by a process for the reductive coupling of nitrobenzene to give azobenzene and azoxybenzene under heterogeneous catalysis by means of a redox catalyst in its reduced or partly reduced form at elevated temperatures in the gas phase, the redox catalyst containing an active metal selected from the group consisting of Bi, V, Cr, Mn, Fe, Co, Pb, Mo, Ce, U, Sn, Sb, Cu, La, W, Nb, Pd, Pt, Ni. In and mixtures of two or more thereof, and, for deoxygenation, nitrobenzene being passed together with at least one gaseous hydrogen-free reducing agent and optionally water over the redox catalyst, wherein the average oxidation state of the active metal of the redox catalyst before the introduction of nitrobenzene together with the reducing agent is at least 0.5 below that maximum oxidation state of the active metal which is stable under the respective reaction conditions.

Steady-state reaction in this context means that a feed containing nitrobenzene and at least one gaseous, hydrogen-free reducing agent, which is preferably selected from the group consisting of carbon monoxide, nitrogen monoxide and sulfur dioxide and mixtures thereof, preferably CO, is passed over the catalyst.

The term at least 0.5 below that maximum oxidation state of the active metal which is stable under the respective reaction conditions means here that the average degree of reduction, measured by means of, for example, ESCA, TPR/TPO (temperature-programmed reduction/temperature-programmed oxidation) and wet-chemical titration, is at least 0.5, preferably at least 1, below that maximum oxidation state of the active metal which is stable under the respective reaction conditions. For bismuth, whose highest oxidation state is +3, this means that its oxidation state is not more than 2.5, preferably not more than 2, when used as an active metal component in the novel process involving a steady-state reaction, before the introduction of the nitrobenzene-containing feed.

This degree of reduction is substantially smaller than that of the catalysts used according to German Laid-Open Application DOS 1,810,828 which can be deduced simply from the fact that, in the novel process, the selectivity with respect to azobenzene and azoxybenzene is substantially higher than in the process according to the above application.

Non-steady-state reaction

We have found that the above objects are achieved in an even more advantageous manner if a non-steady-state reaction is used instead, ie. by a process for the reductive coupling of nitrobenzene to give azobenzene and azoxybenzene under heterogeneous catalysis by means of a redox catalyst in its reduced or partly reduced form at elevated temperatures in the gas phase, the redox catalyst containing at least one active metal selected from the group consisting of Bi, V, Cr, Mn, Fe, Co, Pb, Mo, Ce, U, Sn, Sb, Cu, La, W, Nb, Pd, Pt, Ni, In and mixtures of two or more thereof, wherein the average oxidation state of the active metal of the redox catalyst before the introduction of nitrobenzene is at least 0.5 below that maximum oxidation state of the active metal which is stable under the respective reaction conditions, and, for deoxygenation, nitrobenzene and optionally water is passed over the redox catalyst in the absence of free, gaseous reducing agent and is brought into contact with the redox catalyst in an amount such that this is not completely consumed. Nitrobenzene is reduced by oxygen elimination and the catalyst is oxidized by oxygen uptake.

As indicated above, non-steady-state reaction means in the present case that the reduction of nitrobenzene is carried out in the absence of free gaseous reducing agents over redox catalysts, which contain an active metal component in reduced or partly reduced form, as solid reducing agents which can be regenerated and which act as oxygen acceptors.

After the end of the reduction phase of the nitrobenzene, the consumed, partly oxidized redox catalysts are further reduced in a second step carried out at a different place or a different time, by reduction with a free gaseous reducing agent preferably selected from the group consisting of hydrogen, carbon monoxide, hydrocarbons, eg. methane, ammonia, nitrogen monoxide, sulfur dioxide and nitrobenzene and mixtures thereof, preferably carbon monoxide, hydrogen, methane or nitrobenzene.

In terms of procedure, this catalyst reduction step can be carried out either within the actual process for the reduction of the nitrobenzene or separately therefrom, preferably the cycle of oxidation of the catalyst as a result of the reduction of the nitrobenzene and reduction of the catalyst by free gaseous reducing agent is repeated cyclically in succession so that the total loop is continuous and closed. The redox catalysts which are prereduced but can be regenerated act as oxygen acceptors, so that the initial reaction step consists of deoxy-genation of the nitrobenzene to reactive intermediates, which then dimerize to azobenzene and azoxybenzene.

As described above, the reduced redox catalyst serves both as a catalyst and as an oxygen acceptor in the non-steady-state reaction, with the result that it is converted into a higher oxidation state and has to be reduced again in a regeneration carried out at a different time or in a different place. Accordingly, at least stoichiometric amounts of the redox catalyst are generally required for the reduction.

The non-steady-state reaction as a technical principle per se is part of the prior art and has been described for many oxidation and dehydrogenation reactions:

the oxidation/dehydrogenation reaction is carried out in the absence of free oxidizing agent, ie. oxidizing agent continuously added to the starting material stream, eg.

molecular oxygen or oxygen-containing gases, and instead the redox catalyst consisting of at least one reducible supported metal oxide acts as the sole oxygen source and thus performs the function of an oxygen store. Owing to the release of lattice oxygen during the oxidation/dehydrogenation, the oxidic catalyst is reduced and is therefore consumed in the course of the reaction, so that it has to be regenerated by reoxidation in a second step by means of an oxidizing agent, preferably oxygen-containing gases, including pure oxygen. This general reaction concept for the separation of the two steps of oxidation reactions with the use of a reducible catalyst as a genuine reactant has long been known and was described, for example, for the oxidation or ammoxidation of propylene to acrolein and acrylic acid or acrylonitrile (GB 885 442, GB 999 629, K. Aykan, J. Catal. 12 (1968), 281–290), arsenate and molybdate catalysts being used.

Further oxidation/dehydrogenation processes involving a non-steady-state reaction are described, for example, in the following publications: U.S. Pat. No. 3,440,299, DE 21 18 344, DE 17 93 499, U.S. Pat. No. 3,118,007, GB 840 082, U.S. Pat. No. 4,795,849, DE 35 86 769, U.S. Pat. No. 4,568,789, EP 254 423 and GB 2 156 845.

All these processes involving a non-steady-state reaction relate without exception to oxidation or dehydrogenation reactions. The redox catalyst serves as an oxygen store.

It is only the applicant itself who claims the non-steady-state reductive deoxygenation of phosphine oxides to phosphines and of nitrobenzene to aniline in P 44 43 360.3.

There are two variants for the technical realization of the non-steady-state reaction concept, ie. separation of the two steps either a) spatially or b) with regard to time.

a) Spatial separation

For example, a moving bed or a circulating fluidized bed with the use of a riser reactor is employed to achieve spatial separation, so that, after resulting reaction products have been separated off, the catalyst particles from the deoxygenation zone are transported to a separate regeneration reactor in which the reduction of the catalyst is carried out. The regenerated catalyst is recycled to the deoxygenation zone.

In this preferred embodiment, the process is continuous and cyclic since the catalyst is continuously circulated. The catalyst is subjected to high mechanical stresses and must therefore have sufficient hardness.

Figure 1:
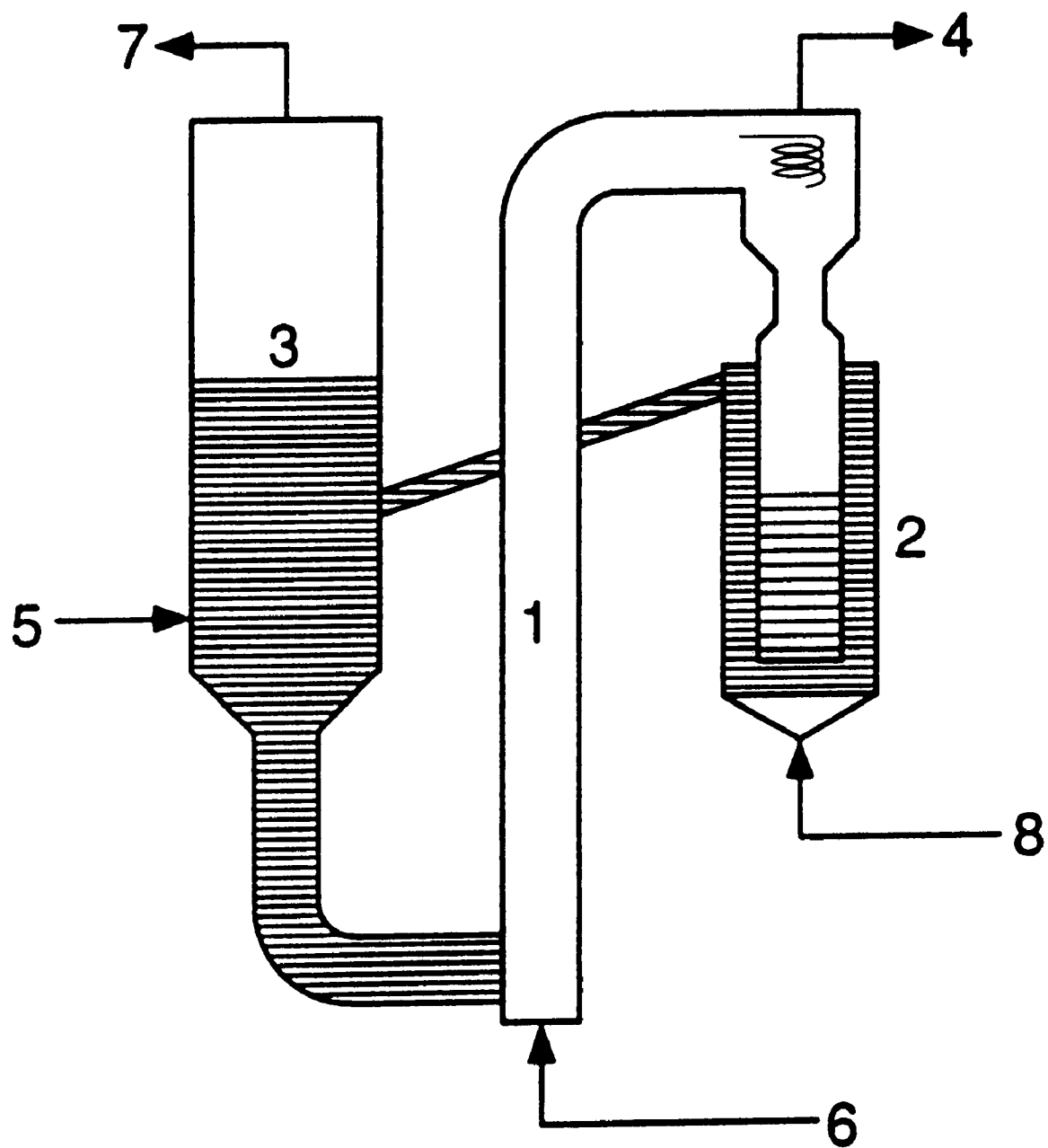
FIG. 1 is a schematic representation of the non-steady state reaction of the present invention.

This embodiment of the novel process with non-steady-state reaction is shown schematically in FIG. 1. There, (1) denotes the riser, (2) the separation apparatus for separating the reduced product (4) from the consumed catalyst and (3) the regenerator in which the consumed catalyst is reduced again by treatment with a reducing agent (5).

The starting material to be reduced (in this case nitrobenzene) enters via a feed means (6). The waste gas leaves the system through the orifice (7). An inlet (8) permits any required feeding of inert gas.

b) Separation with regard to time

Separation with regard to time can be achieved, for example in a fixed catalyst bed, preferably in a tube reactor in which there is essentially no back-mixing, by a procedure in which the reactor is periodically loaded with the compound to be deoxygenated and with the regeneration gas by switching over, intermediate flushing with inert gas also being possible. When a plurality of reactors are used, the switching over or onward switching is carried out in a particularly simple manner so that the reduction of nitrobenzene and the regeneration can take place continuously and in parallel.

Figure 2:
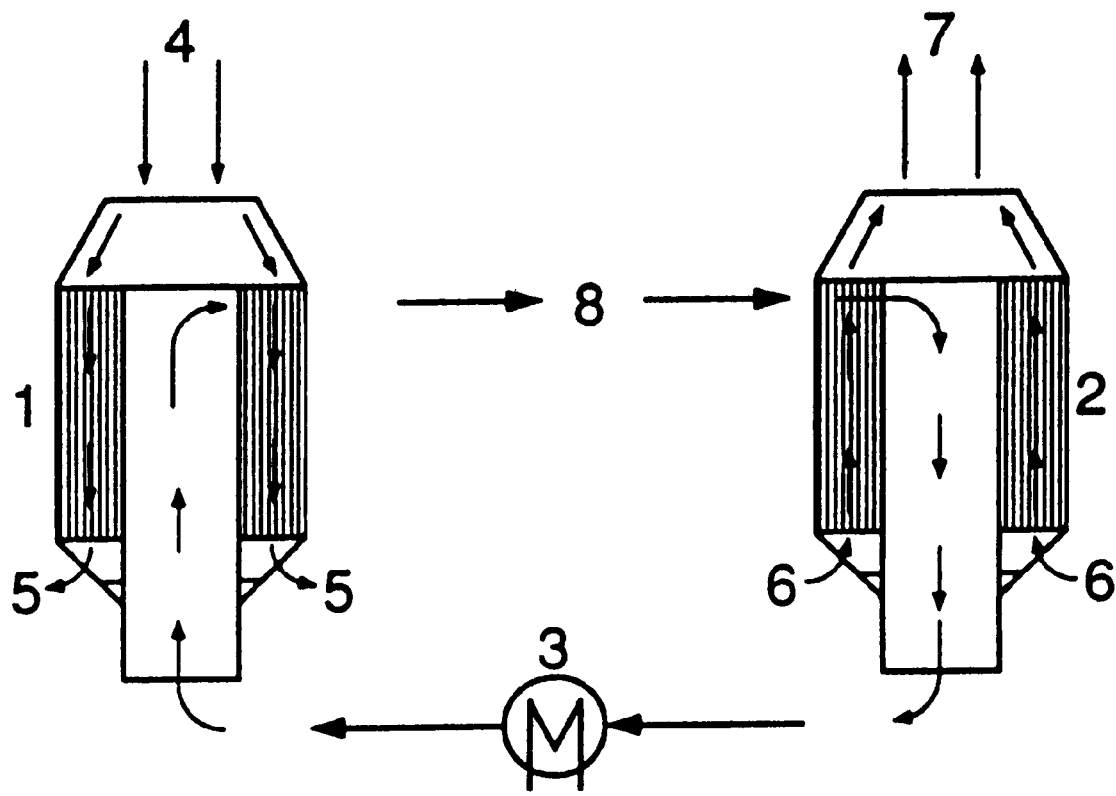
FIG. 2 is a schematic representation of a reaction of the present invention using a fixed bed catalyst.

This embodiment is illustrated in FIG. 2. Fixed-bed reactors in the form of tube-bundle reactors are shown there. While the actual reduction reaction takes place and the product is produced in reactor (1), the regeneration of the consumed redox catalyst with a gaseous, free reducing agent takes place in reactor (2). (3) denotes a heat exchanger. In this embodiment, the nitrobenzene to be reduced is fed in at (4). The product, in this case a mixture of azobenzene and azoxybenzene, leaves the reactor through the outlet (5). In the regeneration reactor (2), the reducing agent (regeneration gas) enters through the inlet (6) and leaves the reactor as waste gas through the outlet (7). (8) represents an integrated heating system.

The non-steady-state reaction, ie. the avoidance of an equilibrium by maintaining a reaction gradient—in this case the gradient of the reduction activity of the redox catalyst with avoidance of back-mixing—is preferably achieved by maintaining pipe (plug) flow and by virtue of the fact that still unused catalyst, ie. catalyst which is unoxidized and thus still has reduction activity, is present at the outlet of the reduction zone.

Catalysts

The redox catalyst used in the novel process, in both the steady-state and the non-steady-state reaction, contains at least one active component capable of a change of oxidation state, preferably a reducible active metal oxide, the active metal being selected from the group consisting of Bi, V, Cr, Mn, Fe, Co, Pb, Mo, Ce, U, Sn, Sb, Cu, La, W, Nb, Pd, Pt, Ni, In and mixtures of two or more thereof.

The reducible active metal oxide can be used either in the form of pure oxide or metal or on a carrier.

The type of carrier is in general not subject to any restrictions, provided that it is inert and has the necessary mechanical strength. It is preferably selected from the group consisting of clays, PILC (pillared clays, zeolites, aluminum phosphates (AlPO), SiC, $Si_3N_4$, Bn, C and/or the metal oxides selected from the group consisting of oxides of the metals Ti, Zr, Zn, Th, Mg, Ca, Ba, Si, Al and mixtures of two or more thereof, furthermore preferably from the group consisting of $TiO_2$, $SiO_2$, $Al_2O_3$, MgO, SiC and $Si_3N_4$.

Application to a carrier increases the surface area and dispersion of the active phase so that high catalyst space velocities are possible.

The redox catalyst may contain further promoters, in particular alkali metals, alkaline earth metals and/or rare earth metals. In particular, the basicity of the catalyst can be established by adding Na, K, Cs or La.

Supported catalysts are preferably used in the novel process since they have the advantage of high mechanical stability to the continuous phase transformations and structural transformations of the active component. The loading of the active component is not particularly limited and is in general from about to about 95, preferably from about 5 to about 50, % by weight, calculated in each case as active metal oxide and based on the total weight of the catalyst. Particularly preferably, the active metal oxide loading is from about 10 to about 30% by weight.

A preferred active metal is Bi and preferred carriers are $TiO_2$, $SiO_2$ and $ZrO_2$.

Accordingly, the novel process is preferably carried out using a redox catalyst which contains Bi as active metal.

Furthermore, a Bi-containing supported catalyst is used as a redox catalyst, the carrier being selected from the group consisting of $TiO_2$, $SiO_2$, $Al_2O_3$, MgO, SiC and $Si_3N_4$.

A redox catalyst containing Bi on $TiO_2$ is particularly preferably used, the Bi content, calculated as $Bi_2O_3$, being from about 5 to about 50% by weight.

Since Bi is basic, the catalyst has only a small tendency to coking and to the formation of cracked products. In the case of acidic systems, on the other hand, losses would occur as a result of coking and crack reactions.

Bi is particularly suitable because bismuth oxides can be readily reduced with $H_2$ or with CO to give considerable amounts of elemental metal even at relatively low temperatures of about 300° C. and at relatively low pressures of $1 \times 10^5$ Pa, ie. can be converted in a simple manner into the reduced or partly reduced state required for carrying out the novel processes. Thus, the deoxygenation and regeneration can advantageously be operated virtually isothermally, this being likely to be an essential precondition for economical operation.

In the novel processes, a prereduction of the catalyst at atmospheric pressure with a free gaseous reducing agent can be effected, ie. there is no need for an expensive procedure at superatmospheric pressure.

Since the novel redox catalysts are prereduced to a low state, ie., before the introduction of nitrobenzene, the active metal has an average oxidation state which is at least 0.5 below that maximum oxidation state of the active metal which is stable under the respective reaction conditions, so that, for example in the case of the preferred Bi-containing catalysts under the reaction conditions present here, considerable amounts of Bi in the oxidation state 0, ie. as elemental, finely divided metal, are present, the nitrobenzene losses due to total oxidation to $CO_x$ and $H_2O$ are negligible since the oxidation potential of redox metals in their (virtually) lowest oxidation state is very small.

The catalyst can be prepared by all known processes, for example by dry blending, impregnation, steeping, precipitation, coprecipitation, spray drying, spray impregnation, suspension, evaporating down or coating. Suitable catalyst precursors are the oxides, hydroxides, carbonates, nitrates, complex compounds with inorganic or organic chelating agents, salts or inorganic and organic acids and organometallic compounds. Further additives, for example pore formers, may also be added. These catalyst precursors are converted into the active catalyst form by suitable heat treatment, generally together with the reductive activation.

It is clear that the redox catalysts have deoxygenation activity only when the active metal is not in its highest oxidation state but is present in at least partly reduced form, as defined above. In the case of Bi as active metal, the bismuth oxides formed during the deoxygenation by oxygen uptake are reduced with $H_2$ at from 250 to 500° C., preferably virtually to metallic Bi. In this case, the active phase at the beginning of the reaction consists of finely divided Bi metal, which is preferably applied to a carrier having a large surface area. With progressing reaction time during the deoxygenation, the catalyst is increasingly oxidized by oxygen uptake and its activity therefore decreases, and the conversion falls. As a consequence of this deactivation behavior, the yield of the desired product generally passes through a flat maximum or a plateau and then decreases monotonically, as a function of the duration of the experiment. In industry, the procedure is not continued until complete deactivation of the catalyst, but the regeneration is initiated beforehand when the yield or conversion has fallen to a certain value, preferably when the yield has fallen 10–20% below the maximum value, or the selectivity decreases.

The maximum change of oxidation state of the active metal thermodynamically possible at the respective reaction temperature (eg. Bi (0) $\leftrightarrows$ Bi (III) or V (III) $\leftrightarrows$ V (V) at about 400° C. and 500° C., respectively) is thus not completely passed through, but the reaction is operated with catalyst utilizations of <1.

The catalyst is used in piece form in a fixed bed, for example in the form of extrudates, rings, annular pellets, granules or chips, spheres, solid pellets or nets having dimensions of from about 0.5 to about 20 mm.

On the other hand, fine particles having high mechanical strength and sizes of from about 0.01 to about 0.9 mm, preferably from about 0.05 to about 0.5 mm, are appropriate for use of the catalyst in a moving or fluidized bed.

Deoxygenation and regeneration

The deoxygenation by the novel process is carried out at reaction temperatures of from 50 to 500° C., preferably from 100 to 400° C., during residence times of from about 0.01 to 100 s, preferably from about 0.1 to about 50 s, at pressures of from about $10^4$ to $10^7$ Pa, preferably from $5 \times 10^4$ to $2 \times 10^6$ Pa, and with a WHSV (Weight Hourly Space Velocity) of from 0.01 to 20, preferably from 0.05 to 10, kg of nitrobenzene per kg of catalyst per h.

In addition to the starting material to be deoxygenated, diluents, for example $CO_2$, $N_2$, noble gases or the hydrogen-free regeneration gas (reducing agent) or mixtures thereof, may be present in the feed.

The regeneration (reduction) of the consumed, completely or partly oxidized catalyst is carried out at from 100 to 1000° C., preferably from 150 to 700° C., particularly preferably from 150 to 600° C., with a free gaseous reducing agent, preferably with $H_2$, CO, a hydrocarbon, $NH_3$, NO, $SO_2$ or nitrobenzene itself (autoredox mode) or a mixture of two or more thereof, particularly preferably with CO, $H_2$ or $CH_4$. Here too, the reactor feed may contain diluents. The regeneration can be operated at reduced, atmospheric or superatmospheric pressure. Pressures of from about 100 mbar to about 20 bar are preferred.

Reactive gas mixtures which liberate the actual reducing agent only in the reactor by chemical reaction are also suitable as regeneration gases. For example, the catalyst may additionally be doped with Cu and $CO/H_2O$ may be used as the regeneration gas. Hydrogen is then formed by an in situ conversion reaction (water-gas shift reaction) at the Cu center and is capable of reducing the metal oxide.

Instead of the nitrobenzene, nitrobenzenes which are substituted on the nucleus and may have up to five, preferably up to three, further substituents may be used in the novel process, particular example of substituents being halogen, preferably chlorine, fluorine or bromine, a nitrile group, amino, alkyl, preferably $C_1$–$C_8$-alkyl, cycloalkyl, alkenyl, preferably $C_1$–$C_8$-alkenyl, cycloalkenyl, alkoxy, preferably $C_1$–$C_6$-alkoxy, or unsubstituted or substituted phenyl, which may in turn be substituted as defined above.

Fused aromatic nitro compounds, for example nitronaphthalenes and nitroheterocycles, may also be used.

Examples of nitrobenzenes which are substituted on the nucleus and are particularly preferably used in the present invention are:

o-, m- and p-nitrotoluene;

1,2-dimethyl-3-nitrobenzene, 1,2-dimethyl-4-nitrobenzene, 1,3-dimethyl-2-nitrobenzene, 1,3-dimethyl-4-nitrobenzene, 1,3-dimethyl-5-nitrobenzene and 1,4-dimethyl-2-nitrobenzene;

2-, 3- and 4-nitroanisole;

o-, m- and p-nitroaniline, 2,4- and 2,6-dinitroaniline;

2-methyl-3-nitroaniline, 2-methyl-4-nitroaniline, 2-methyl-5-nitroaniline, 2-methyl-6-nitroaniline, 3-methyl-2-nitroaniline, 3-methyl-4-nitroaniline, 3-methyl-5-nitroaniline, 3-methyl-6-nitroaniline, 4-methyl-2-nitroaniline and 4-methyl-3-nitroaniline;

1,2-, 1,3- and 1,4-dinitrotoluene;

nitronaphthalenes, eg. 1- and 2-nitronaphthalene, and dinitronaphthalenes, eg. 1,5- and 1,8-dinitronaphthalene;

o-, p- and m-dinitrobenzene, 2,4- and 3,5-dinitrotoluene, 1,3-dimethyl-2,4-dinitrobenzene, 1,3-dimethyl-2,5-dinitrobenzene and 1,3-dimethyl-2,6-dinitrobenzene;

chlorinated nitrobenzenes, eg. o-, m- and p-chloronitrobenzene, 1,4-dichloro-2-nitrobenzene, 1,2-dichloro-3-nitrobenzene, 1,2-dichloro-4-nitrobenzene, 1-chloro-2,4-dinitrobenzene, 2-chloro-1,3-dinitrobenzene, 1-chloro-2,4-dinitrobenzene and 2,4,5-trichloro-1-nitrobenzene;

chloronitrotoluenes, eg. 2-chloro-4-nitrotoluene, 4-chloro-2-nitrotoluene, 2-chloro-6-nitrotoluene, 3-chloro-4-nitrotoluene and 4-chloro-3-nitrotoluene; and 3-chloro-2-nitroaniline, 4-chloro-2-nitroaniline, 5-chloro-2-nitroaniline, 2-chloro-6-nitroaniline, 2-chloro-3-nitroaniline, 4-chloro-3-nitroaniline, 3-chloro-5-nitroaniline, 2-chloro-5-nitroaniline, 2-chloro-4-nitroaniline and 3-chloro-4-nitroaniline.

Among these, the alkylnitrobenzenes and toluidines (methylnitroanilines) are particularly preferably used.

It has been found that carrying out the process of the present invention in the presence of water results in a further improved nitrobenzene conversion with a high selectivity for the production of azobenzene and azoxybenzene. It was surprisingly found that despite the addition of water as a proton donator essentially no aniline is formed.

The reason for the further improvement of the process has not been clarified yet, it may, however, be attributed to the fact that the addition of water constantly washes off high-boiling products from the catalyst surface, which is then in turn available for the activation of nitrobenzene.

When carrying out the process according to the invention with the addition of water to the nitrobenzene feed, the ratio of the volume flows of nitrobenzene and water (in the liquid state) lies preferably within the range of about 10:1 to about 1:10, more preferably about 1:1 to about 1:7.

The present invention furthermore relates to the redox catalyst itself, as defined above, the catalysts classed as being preferably usable in the description of the process likewise being preferred embodiments of the novel catalyst.

EXAMPLES

The cutting hardness stated in the Examples below was determined as follows:

The cutting hardness was measured on an apparatus from Frank, type No. 81557. The measuring range was from 0 to 200 N. The test speed was 8 mm/min. The cutting knife had a length of 15 mm and a height of 10 mm. Before every measurement series, each of which consisted of twenty individual measurements, the zero point was adjusted or checked.

For the actual measurement, an extrudate was in each case placed transverse to the knife, on the disk provided for this purpose (midpoint) and the cutting hardness was determined as stated by the manufacturer, the cutting hardness being displayed on the apparatus directly in N (unit N/extrudate).

Example 1

Catalyst preparation 14.6 g of $Bi(NO_3)_3 \cdot 5H_2O$ were dissolved in distilled water with the addition of 10 ml of concentrated $HNO_3$ and the solution was brought to a total volume of 65 ml. The solution was divided. The $TiO_2$ carrier of type DT-51 (Rhône-Poulenc) in the form of 4 mm extrudates was impregnated twice with 32.5 ml of the above solution per impregnation step. Calcination was carried out for 16 hours at 160° C. and for 2 hours at 550° C. Light beige extrudates were obtained. The catalyst had a formal composition of 6.7% by weight of $Bi_2O_3$ and 93.3% by weight of $TiO_2$.
BET surface area×65.7 $m^2/g$
Cutting hardness×31 N/extrudate The extrudates were converted into chips and a chip fraction of from 0.5 to 0.71 mm was separated off by sieving.

Reactor experiments with a non-steady-state reaction were then carried out using the catalyst thus prepared. For this purpose, the experiments for the reductive coupling of nitrobenzene were carried out in a helical tube reactor which contained 20 ml of catalyst and was heated from the outside by a liquid salt melt so that virtually isothermal conditions were present.

A 0.5–0.71 mm chip fraction of the catalyst was initially taken (weight 18.4 g).

The fixed catalyst bed was first prereduced with $H_2$ for 1 hour at the reaction temperature and then flushed with $N_2$ gas. Thereafter, nitrobenzene which had been converted beforehand into the gas phase in an evaporator and diluted with $N_2$ carrier gas was passed over the bed in the absence of free reducing agent. The residence time was established by the controlled flow of the $N_2$ carrier gas. A further flushing phase with $N_2$ carrier gas followed. This cycle was repeated continuously. The deoxygenation phase and the regeneration phase were each carried out at the same reactor temperature for each cycle.

The integral condensable reactor discharge was collected in a cold trap. After each cycle, the catalyst bed and the lines on the reactor outlet side were flushed with ethanol/acetone, the flushing solution was combined with the contents of the cold trap and the total solution thus obtained was analyzed by GC-MS. The products still adhering to the catalyst and the solid discharge deposited in the lines were also analyzed in this manner.

The results for the reaction are shown in Table 1.

It can be seen that good yields of azobenzene and azoxybenzene were obtained in combination with high nitrobenzene conversions.

The catalyst was operated over 36 cycles altogether without deactivation phenomena being observable.

TABLE 1

Abbreviations: NB = nitrobenzene, AB = azobenzene, AOB = azoxybenzene, NOB = nitrosobenzene, RET = residence time
Overall GC-MS analysis of the integral reactor liquid and solid discharge and the catalyst deposits per cycle (by flushing out the lines and condenser and the reactor/catalyst bed with ethanol after each cycle and combining the solution with the liquid discharge), but still without gasification and coking.

| | Feed | | | | | Product distribution | | | |
|---|---|---|---|---|---|---|---|---|---|
| Cycle | NB (ml/h) | N$_2$ carrier gas (l(S.T.P.)/h) | Run time (min) | T (°C.) | RET (s) | NB | Aniline | AB | AOB | NOB |
| | | | | | | (GC % by area) | | | | |
| 30 | 8 | 10 | 20 | 300 | 2.9 | 48.7 | 14.2 | 17.6 | 5.6 | 0.5 |
| 31 | 8 | 10 | 20 | 300 | 2.9 | 57.2 | 12.5 | 18.2 | 4.8 | 1.6 |
| 32 | 8 | 10 | 15 | 340 | 2.9 | 55.9 | 24.3 | 11.2 | — | — |
| 33 | 8 | 10 | 15 | 340 | 2.9 | 55.8 | 11.7 | 13.9 | — | 0.7 |
| 34 | 8 | 10 | 15 | 340 | 2.9 | 54.3 | 12.1 | 18.9 | 0.7 | 2.8 |
| 35 | 8 | 15 | 15 | 360 | 1.9 | 50.0 | 2.3 | 27.9 | 6.4 | 0.3 |
| 36 | 8 | 15 | 15 | 360 | 1.9 | 33.6 | 9.5 | 30.8 | 5.8 | — |

Example 2

Catalyst preparation 83.1 g of basic bicarbonate Bi$_2$CO$_5$ and 225 g of TiO$_2$ powder (type DT-51 from Rhône-Poulenc) were dry blended for 1 hour and then compacted in a kneader with the addition of water and extrusion assistant for 2.5 hours. The kneaded material was molded in an extruder to give 3 mm solid extrudates. The extrudates were dried for 16 hours at 120° C. and calcined for 2 hours at 550° C. Beige-light yellow extrudates were obtained. A catalyst having the formal composition of 25% by weight of Bi$_2$O$_3$ and 75% by weight of TiO$_2$ was obtained.

BET surface area=42.5 m$^2$/g

Cutting hardness=28 N/extrudate

The extrudates were converted into chips and the chip fraction from 0.6 to 0.71 mm was separated off by sieving.

The conversion of nitrobenzene into azobenzene and azoxybenzene was carried out in the same way as in Example 1, the reactor being filled with 20 ml of chips of the above fraction at the beginning of the reaction.

The results of the reaction are shown in Table 2.

TABLE 2

Abbreviations: NB = nitrobenzene, AB = azobenzene, AOB = azoxybenzene, NOB = nitrosobenzene, RET = residence time
Overall GC-MS analysis of the integral reactor liquid and solid discharge and the catalyst deposits per cycle (by flushing out the lines and condenser and the reactor/catalyst bed with ethanol after each cycle and combining the solution with the liquid discharge), but still without gasification and coking.

| | Feed | | | | | Product distribution | | | |
|---|---|---|---|---|---|---|---|---|---|
| Cycle | NB (ml/h) | N$_2$ carrier gas (l(S.T.P.)/h) | Run time (min) | T (°C.) | RET (s) | NB | Aniline | AB | AOB | NOB |
| | | | | | | (GC % by area) | | | | |
| 15 | 8 | 15 | 10 | 340 | 1.9 | 17.3 | 17.2 | 24.2 | 1.3 | — |
| 16 | 8 | 15 | 10 | 340 | 1.9 | 21.8 | 10.1 | 18.4 | 13.7 | 1 |
| 17 | 8 | 15 | 10 | 340 | 1.9 | 31 | 5.8 | 22.2 | 6.1 | 2.3 |
| 18 | 8 | 15 | 10 | 320 | 1.9 | 29 | 4.7 | 28.2 | 22.8 | — |
| 19 | 8 | 15 | 10 | 320 | 1.9 | 21.3 | 9.8 | 32.8 | 14.6 | — |
| 20 | 8 | 15 | 10 | 320 | 1.9 | 54.4 | 3.5 | 17.4 | 4.6 | — |
| 21 | 8 | 15 | 10 | 300 | 1.9 | 37.2 | 2.8 | 26.1 | 12.5 | 0.8 |
| 22 | 8 | 15 | 10 | 300 | 1.9 | 44.6 | 1.3 | 20.1 | 9.6 | 2.9 |
| 23 | 8 | 15 | 10 | 300 | 1.9 | 12.4 | 6.4 | 40.7 | 1.9 | — |
| 24 | 8 | 15 | 10 | 300 | 1.9 | 26.9 | 5.3 | 39.3 | 0.6 | 0.5 |
| 25 | 8 | 15 | 10 | 280 | 1.9 | 56.8 | 1.4 | 15.7 | 7.5 | 1.6 |
| 26 | 8 | 15 | 10 | 280 | 1.9 | 47.4 | 2 | 24.5 | 7.1 | 1.3 |
| 27 | 8 | 15 | 10 | 260 | 1.9 | 60.2 | 1.5 | 17.8 | 12 | 0.2 |
| 28 | 8 | 15 | 10 | 260 | 1.9 | 37.9 | 1 | 29.2 | 20.6 | 0.8 |

Example 3

A conversion analogous to Example 1 was carried out by using the catalyst according to Example 2, wherein instead of nitrobenzene a mixture of nitrobenzene and water, which had been converted beforehand into the gas phase in an evaporator and diluted with N$_2$ carrier gas, was passed over the bed in the absence of free reducing agent.

Apart from that, the conversion was carried out in the same manner as Example 1.

The results for the reaction are shown in Table 3.

It is apparent that at very high nitrobenzene conversion good yields of azobenzene and azoxybenzene are obtained and that the addition of water to the nitrobenzene feed has a favorable influence on the activity and selectivity.

The catalyst was operated over 48 cycles altogether without deactivation phenomena being observable.

TABLE 3

Abbreviations: NB = nitrobenzene, AB = azobenzene, AOB = azoxybenzene, NOB = nitrosobenzene
Overall GC-MS analysis of the integral reactor liquid and solid discharge and the catalyst deposits per cycle (by flushing out the lines and condenser and the reactor/catalyst bed with ethanol after each cycle and combining the solution with the liquid discharge), but still without gasification and coking. The portions missing in the product distribution essentially consist of components which are higher boiling compared to the listed products.

| | Feed | | | | | Product distribution | | | | |
|---|---|---|---|---|---|---|---|---|---|---|
| Cycle | NB (ml/h) | $H_2O$ (ml/h) | $N_2$ carrier gas (l(S.T.P.)/h) | Run time (min) | T (°C.) | NB | Aniline | AB | AOB | NOB |
| | | | | | | (GC % by area) | | | | |
| 39 | 8 | 1 | 25 | 5 | 260 | 16.5 | 11.8 | 13.5 | — | |
| 40 | 8 | 2 | 25 | 5 | 260 | 19.9 | 10.2 | 43.6 | 2.8 | |
| 41 | 8 | 4 | 25 | 5 | 260 | 47.6 | 2.9 | 23.7 | 15.2 | — |
| 42 | 8 | 8 | 25 | 5 | 260 | 19 | 5.9 | 50.7 | 14.8 | — |
| 43 | 8 | 10 | 25 | 5 | 260 | 10.3 | 4.7 | 53.9 | 16.6 | — |
| 44 | 8 | 12 | 25 | 5 | 260 | 28.9 | 3.2 | 39.7 | 17 | — |
| 45 | — | — | — | — | — | — | — | — | — | — |
| 46 | 8 | 20 | 25 | 5 | 260 | 1.3 | 4.6 | 68.3 | — | — |
| 47 | 8 | 30 | 25 | 5 | 260 | 5.5 | 6.8 | 59.3 | 18.2 | — |
| 48 | 8 | 50 | 25 | 5 | 260 | 13.1 | 6.3 | 57.3 | 13.1 | — |

We claim:

1. A process for the deoxygenation of unsubstituted or substituted nitrobenzene to unsubstituted or substituted azobenzene and unsubstituted or substituted azoxybenzene which is carried out at elevated temperatures in the gas phase in the presence of a heterogeneous catalyst, wherein the nitrobenzene is passed over the heterogeneous redox catalyst in the absence of a free, gaseous reducing agent, and in an amount such that said redox catalyst is not completely consumed, and wherein the heterogeneous catalyst contains at least one active metal selected from the group consisting of Bi, V, Cr, Mn, Fe, Co, Pb, Mo, Ce, U, Sn, Sb, Cu, La, W, Nb, Pd, Pt, Ni, In and mixtures of two or more thereof, the average oxidation state of the active metal of the redox catalyst prior to the introduction of the nitrobenzene being at least 0.5 below the maximum oxidation state of the active metal which is stable under the respective reaction conditions.

2. The process defined in claim 1, wherein the nitrobenzene is substituted on the nucleus.

3. The process defined in claim 1 which is carried out continuously, alternately with a reductive regeneration of the redox catalyst.

4. The process defined in claim 3, wherein a change between deoxygenation and reductive regeneration of the redox catalyst is effected by using a fixed catalyst bed which is loaded periodically with nitrobenzene and the regeneration gas.

5. The process defined in claim 3, wherein a change between deoxygenation and reductive regeneration of the redox catalyst is effected by introducing mobile catalyst particles, with the use of a moving bed or of a circulating fluidized bed, alternately into a deoxygenation reactor and into a regeneration reactor separated therefrom.

6. The process defined in claim 1 wherein the consumed redox catalyst is regenerated by bringing it into contact with at least one gaseous reducing agent, selected from the group consisting of hydrogen, carbon monoxide, hydrocarbons, ammonia, nitrogen monoxide, sulfur dioxide and nitrobenzene and mixtures of two or more thereof, at elevated temperatures.

7. The process defined in claim 1 wherein at least one active metal is Bi.

8. The process defined in claim 1 wherein the active metal component of the redox catalyst is applied to a carrier which is selected from the group consisting of clays, zeolites, $AlPO_4$, SiC, $Si_3N_4$, BN, C and a metal oxide selected from the group consisting of the oxides of the metals Ti, Zr, Zn, Th, Mg, Ca, Ba, Si and Al and mixtures of two or more thereof.

9. The process defined in claim 8, wherein the carrier is selected from the group consisting of $TiO_2$, $SiO_2$, $Al_2O_3$, MgO, SiC, $Si_3N_4$ and $ZrO_2$.

10. The process defined in claim 1 which is carried out in the presence of water.

* * * * *